US008721666B2

(12) United States Patent
Schroeder et al.

(10) Patent No.: US 8,721,666 B2
(45) Date of Patent: May 13, 2014

(54) METHOD OF FACIAL RECONSTRUCTIVE SURGERY USING A SELF-ANCHORING TISSUE LIFTING DEVICE

(75) Inventors: Jens Schroeder, New York, NY (US); Susanne Landgrebe, Sülfeld (DE); Burkhard Peters, Wattenbek (DE); Barbara Schuldt-Hempe, Bad Bramstedt (DE)

(73) Assignee: Ethicon, Inc., Somerville, NJ (US)

( * ) Notice: Subject to any disclaimer, the term of this patent is extended or adjusted under 35 U.S.C. 154(b) by 1133 days.

(21) Appl. No.: 11/904,198

(22) Filed: Sep. 26, 2007

(65) Prior Publication Data

US 2009/0082791 A1  Mar. 26, 2009

(51) Int. Cl.
*A61B 17/08* (2006.01)
*A61B 17/04* (2006.01)

(52) U.S. Cl.
USPC .......................................... 606/151; 606/228

(58) Field of Classification Search
USPC ................. 606/151, 153, 155, 213, 215, 216, 606/228–232; 623/23.72–23.76, 8; 600/30, 600/37, 208; 128/898; 604/164.01
See application file for complete search history.

(56) References Cited

U.S. PATENT DOCUMENTS

| | | | | |
|---|---|---|---|---|
| 3,646,615 A | * | 3/1972 | Ness | 606/1 |
| 3,833,972 A | * | 9/1974 | Brumlik | 24/449 |
| 4,063,638 A | * | 12/1977 | Marwood | 206/63.3 |
| 5,139,511 A | * | 8/1992 | Gill et al. | 606/198 |
| 5,217,494 A | | 6/1993 | Coggins et al. | 623/11 |
| 5,611,814 A | | 3/1997 | Lorenc | 606/213 |
| 6,551,343 B1 | * | 4/2003 | Tormala et al. | 606/213 |
| 6,692,499 B2 | * | 2/2004 | Tormala et al. | 606/213 |
| 7,601,164 B2 | * | 10/2009 | Wu | 606/228 |
| 7,607,164 B2 | * | 10/2009 | Vasishth et al. | 726/1 |
| 7,850,700 B2 | * | 12/2010 | Sakura | 606/144 |
| 2002/0029011 A1 | * | 3/2002 | Dyer | 602/41 |
| 2002/0198544 A1 | * | 12/2002 | Uflacker | 606/144 |
| 2003/0088270 A1 | | 5/2003 | Lubbers et al. | 606/213 |

(Continued)

FOREIGN PATENT DOCUMENTS

DE  10 2005 012 555  9/2006
EP  1700579  9/2006

(Continued)

OTHER PUBLICATIONS

EP Exam Report for Application No. 08802672.9—2310 dated Oct. 8, 2012.

(Continued)

*Primary Examiner* — Corrine M McDermott
*Assistant Examiner* — Christopher L Templeton

(57) ABSTRACT

A self-anchoring tissue lifting device for use with facial cosmetic reconstructive surgery includes an implant and a removable foil cover disposed on the implant. The implant includes an elongated mesh strip having a distal end on which is situated a tissue anchoring fleece material. Opposite lateral edges of the mesh material are preferably laser cut during the manufacturing process of the implant to provide a plurality of tissue engaging prickles along the longitudinal length of the implant. For treating the mid face and jowl, a stab incision is made within the hairline of the temple region of the patient and the device is applied from the temporal area to the peak of the ipsilateral cheek to capture the malar fat pad to correct midface abnormalities or the ptotic tissue causing the jowl.

16 Claims, 7 Drawing Sheets

(56) References Cited

U.S. PATENT DOCUMENTS

| | | | |
|---|---|---|---|
| 2003/0149447 A1* | 8/2003 | Morency et al. | 606/228 |
| 2004/0010276 A1 | 1/2004 | Jacobs et al. | 606/153 |
| 2004/0015048 A1 | 1/2004 | Neisz et al. | |
| 2005/0203576 A1* | 9/2005 | Sulamanidze et al. | 606/228 |
| 2005/0261737 A1* | 11/2005 | Sakura | 606/215 |
| 2005/0267531 A1* | 12/2005 | Ruff et al. | 606/228 |
| 2005/0267532 A1* | 12/2005 | Wu | 606/228 |
| 2006/0025649 A1* | 2/2006 | Smith et al. | 600/30 |
| 2006/0025783 A1* | 2/2006 | Smith et al. | 606/139 |
| 2007/0055095 A1* | 3/2007 | Chu et al. | 600/37 |
| 2007/0088274 A1* | 4/2007 | Stubbs et al. | 604/164.01 |
| 2007/0156175 A1* | 7/2007 | Weadock et al. | 606/216 |
| 2007/0173887 A1* | 7/2007 | Sasaki | 606/232 |
| 2008/0082113 A1* | 4/2008 | Bishop et al. | 606/151 |
| 2008/0262542 A1* | 10/2008 | Sulamanidze et al. | 606/228 |

FOREIGN PATENT DOCUMENTS

| | | |
|---|---|---|
| JP | 2005-532848 A | 11/2005 |
| WO | WO 03/070088 | 8/2003 |
| WO | WO 2006/005144 A1 | 1/2006 |
| WO | WO 2006/099703 A2 | 9/2006 |

OTHER PUBLICATIONS

JP Notice of Rejection for Patent Application 2010-526219 dated Mar. 5, 2013. (Translated copy).

* cited by examiner

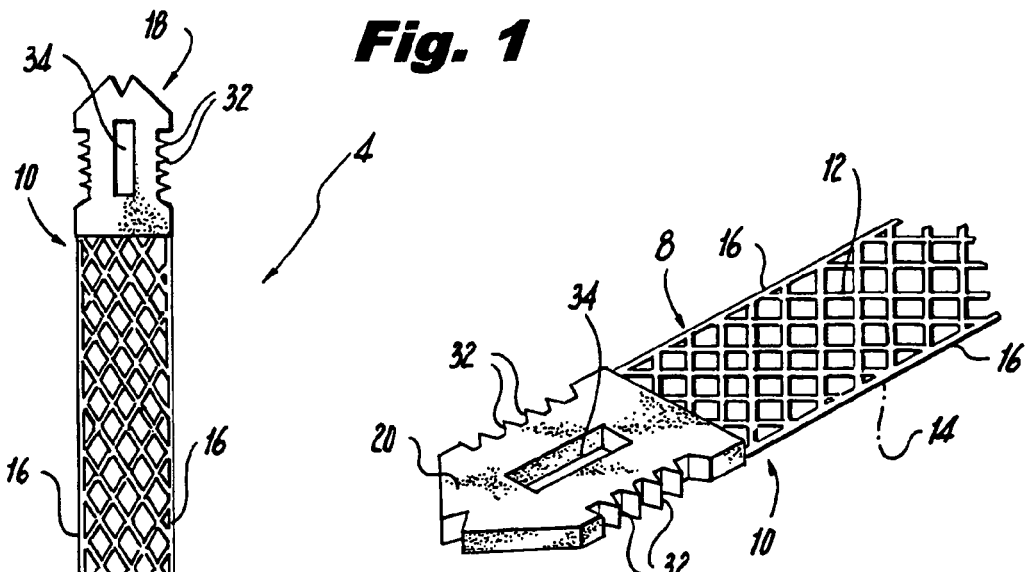
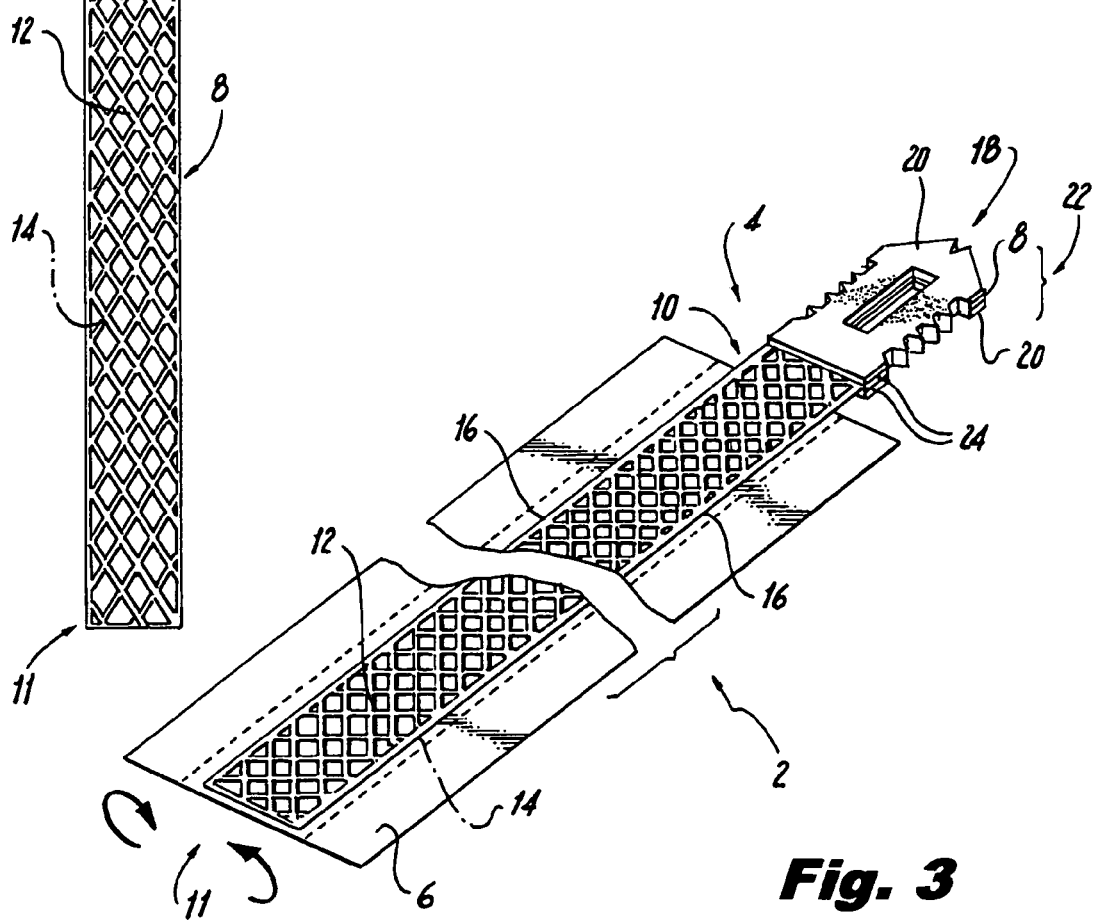

Fig. 6A
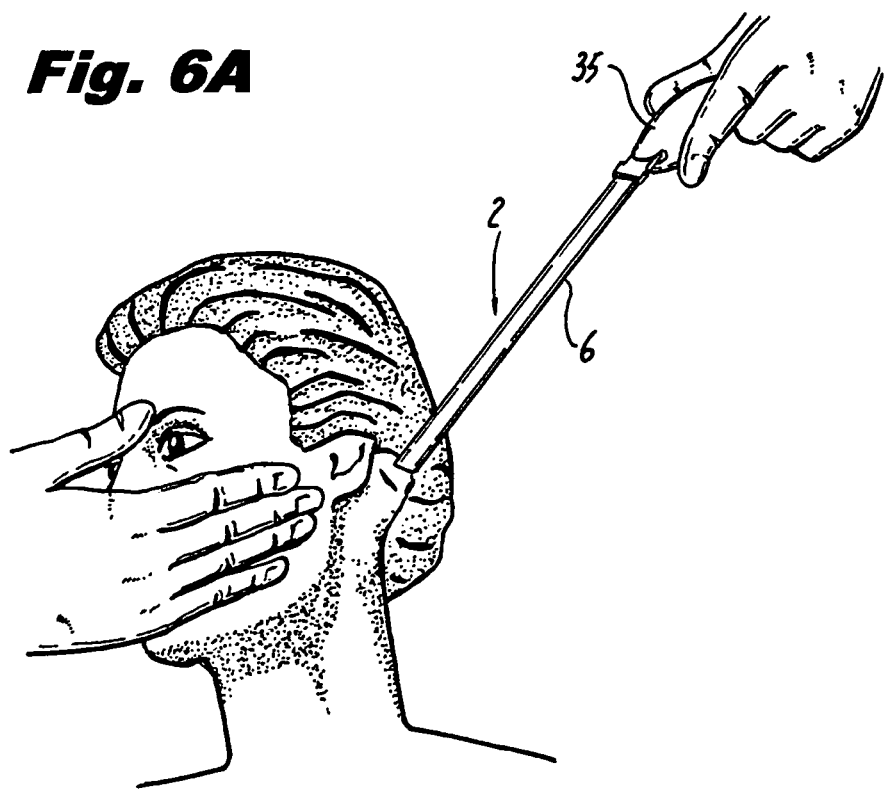
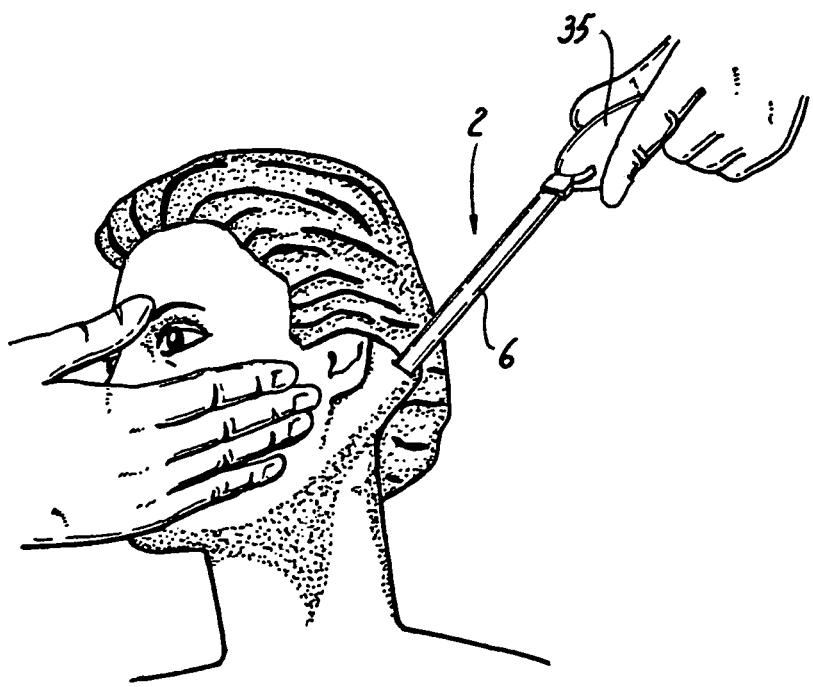
Fig. 6B

Fig. 6C
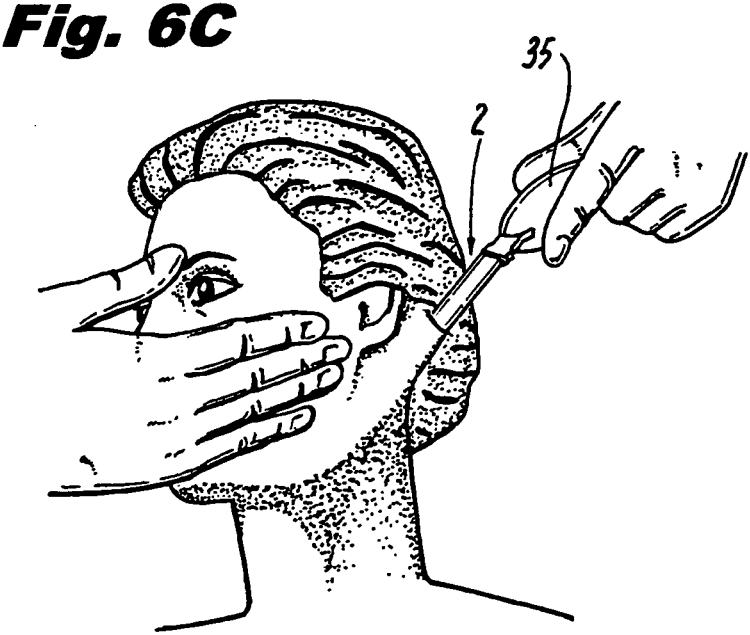
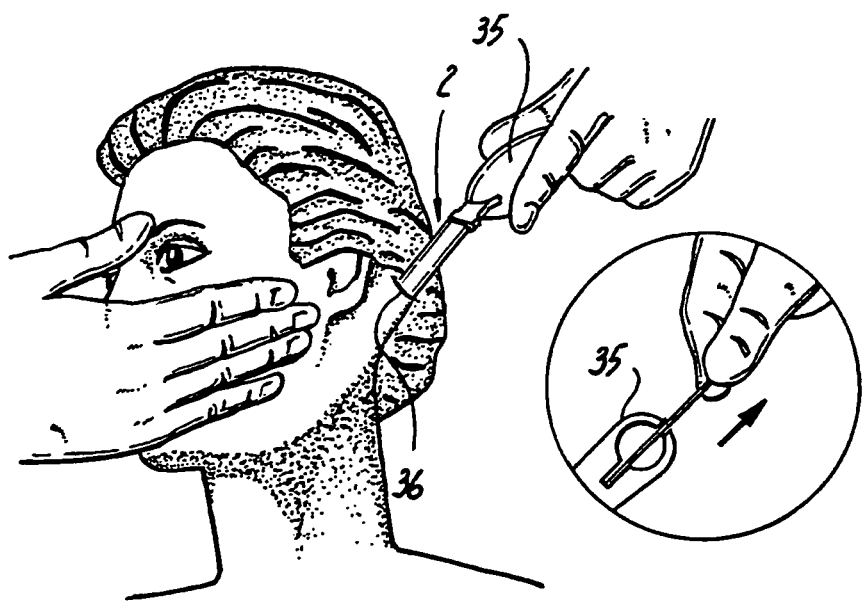
Fig. 6D

Fig. 6E
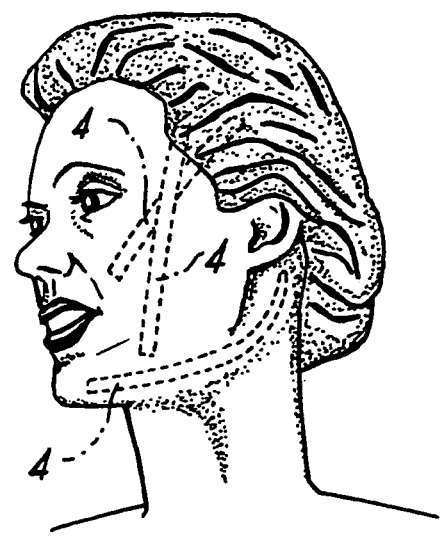
Fig. 6F

METHOD OF FACIAL RECONSTRUCTIVE SURGERY USING A SELF-ANCHORING TISSUE LIFTING DEVICE

BACKGROUND OF THE INVENTION

1. Field of the Invention

This invention generally relates to methods and apparatus for cosmetic reconstructive surgery, and more particularly relates to implantable devices for use with facial cosmetic reconstructive surgery.

2. Description of the Prior Art

Accurate rejuvenation of the aging face depends not only on proper preoperative analysis of the deformities involved in each patient, but also on the proper choice of techniques utilized to adequately address each of the contributing anatomical factors. Currently, various procedures are established in the field of facial cosmetic surgery, each addressing a specific problem. For example, chemical peels, Botox™ and filler injections improve cutaneous structure. Minimally invasive and other surgical procedures, such as face lift procedures including brow-forehead lifts, midface lifts and neck lifts, address excesses of skin. The aforementioned techniques are the only known procedures for reshaping and re-contouring the face of a patient suffering from soft tissue ptosis (the drooping of the eyelids or other tissue).

Patients suffering from forehead and midface region abnormalities may be treated with minimally invasive procedures such as endoscopic lifts and suture suspensions. Both methods have varying success rates. No method is conventionally available to successfully treat abnormalities originating in the cervical (neck) region. The conventional methods of facial cosmetic surgery fail in the cervical region for a variety of reasons, mainly due to the motility of the neck in addition to the thick, floppy soft tissue sheath that is unsupported by bony structure.

The present invention cosmetically improves the outcome of surgical treatment for rejuvenation of the midface, jowl, and cervical areas using a novel mesh tape that simplifies the surgical procedure, decreases its invasiveness and decreases the severity and duration of the post operative rehabilitation period.

OBJECTS AND SUMMARY OF THE INVENTION

It is an object of the present invention to provide a self-anchoring tissue lifting device and method of facial reconstructive surgery which improve the cosmetic outcome of facial reconstructive procedures.

It is another object of the present invention to provide a self-anchoring tissue lifting device and method of facial reconstructive surgery which simplify facial reconstructive surgeries.

It is yet another object of the present invention to provide a self-anchoring tissue lifting device and method of facial reconstructive surgery which decrease the invasiveness of facial reconstructive surgeries.

It is still another object of the present invention to provide a self-anchoring tissue lifting device and method of facial reconstructive surgery which may be successfully used in the cervical region of a patient.

It is a further object of the present invention to provide a self-anchoring tissue lifting device and method of facial reconstructive surgery which prevent the formation of a scar plate.

It is yet a further object of the present invention to provide a self-anchoring tissue lifting device and method of facial reconstructive surgery which provide reliable and durable lift of human facial tissue.

It is still a further object of the present invention to provide a self-anchoring tissue lifting device and method of facial reconstructive surgery which prevent visualization and tactile sensation of the implantable device.

It is yet a further object of the present invention to provide a self-anchoring tissue lifting device which may be readily adaptable to conform and adjust to a selected region of human tissue.

It is still another object of the present invention to provide a self-anchoring tissue lifting device and method of facial reconstructive surgery which overcome the inherent disadvantages of known facial cosmetic reconstructive surgery methods and apparatus.

The present invention is a self-anchoring tissue lifting device and method of use for the treatment of facial abnormalities and deformities. The device basically includes an implant and a removable foil cover disposed on the implant.

The implant preferably includes an elongated, relatively thin, generally planar, mesh main body or strip having a distal end and a proximal end situated longitudinally opposite the distal end, opposite top and bottom surfaces and opposite lateral edges, each of which is situated along the longitudinal length of the mesh strip between the distal end and the proximal end thereof. The distal end of the mesh strip includes a tissue fixation tip mounted thereon.

The tissue fixation tip may be in the form of a fleece material, such as that commonly referred to by the trademark ETHISORB® manufactured by Ethicon GmbH, Norderstedt which can become affixed to tissue of a patient upon its contact therewith. The proximal end of the mesh strip preferably has no tissue fixation tip situated thereat, like that at the distal end, other than the mesh material itself. The opposite lateral edges of the mesh material are preferably laser cut during the manufacturing process of the implant to provide a plurality of tissue engaging "prickles" along the longitudinal length of the implant.

The removable foil cover wraps about the implant at least along a portion of the longitudinal length of the mesh strip thereof, to prevent the adhesion of the implant to the patient's body tissue during the initial phases of the deployment and proper positioning of the implant.

For treating a patient's midface and jowl, using the self-anchoring tissue lifting device of the present invention, a stab incision is made within the hairline of the temple region of the patient, and the device is applied from the temporal area to the peak of the ipsilateral cheek to capture the malar fat pad (to correct midface abnormalities) or the ptotic tissue causing the jowl. For treating the neck area, the device is applied to a stab incision through the subcutaneous tissue plane from behind the ear to the ipsilateral submental area. The distal end of the implant, having the tissue fixation tip situated thereat, is located in the submental area, that is; the mouth floor close to the chin, while the proximal end of the implant, still covered by the foil cover, resides in a position at the mastoid.

More specifically, and in accordance with the procedure for implanting the device of the present invention, an applicator tool is used to position the self-anchoring tissue lifting device of the present invention in this proper position subcutaneously. When the distal end of the implant having the tissue fixation tip situated thereat is released from the applicator tool and brought under slight tension by some backtracking of the skin, the tissue fixation tip will interlock with the septae (vertical fascias) of the subcutaneous layer.

After the applicator tool has been removed, the foil cover is gradually pulled out while the ptotic soft tissue is shifted according to a vector pointing to a backward and upward direction relative to the patient's face. With the simultaneous tissue shift during the foil cover removal and freeing of the mesh implant, the proximal end of the implant is shifted from its initial position to a more facially upward position and, when uncovered from the foil cover, interlocks with the tissue thereat. Thus, the tissue is captured at or close to its original position.

The self-anchoring tissue lifting device and method of use of the present invention yield cosmetically and structurally superior facial reconstructive surgeries that minimize invasiveness and decrease post-operative rehabilitation periods.

A preferred form of the self-anchoring tissue lifting device and method of its use in facial reconstructive surgery, as well as other embodiments, objects, features and advantages of this invention, will be apparent from the following detailed description of illustrative embodiments thereof, which is to be read in conjunction with the accompanying drawings.

BRIEF DESCRIPTION OF THE DRAWINGS

FIG. 1 is a top view of the self-anchoring tissue lifting device formed in accordance with the present invention.

FIG. 2 is an enlarged perspective view of the distal end of the self-anchoring tissue lifting device formed in accordance with the present invention.

FIG. 3 is another enlarged perspective view of the distal end of the self-anchoring tissue lifting device formed in accordance with the present invention.

FIGS. 6A-6F are a series of pictorial illustrations showing a method of use of the self-anchoring tissue lifting device formed in accordance with the present invention in treating a neck abnormality.

DETAILED DESCRIPTION OF THE PREFERRED EMBODIMENTS

Figure 4:
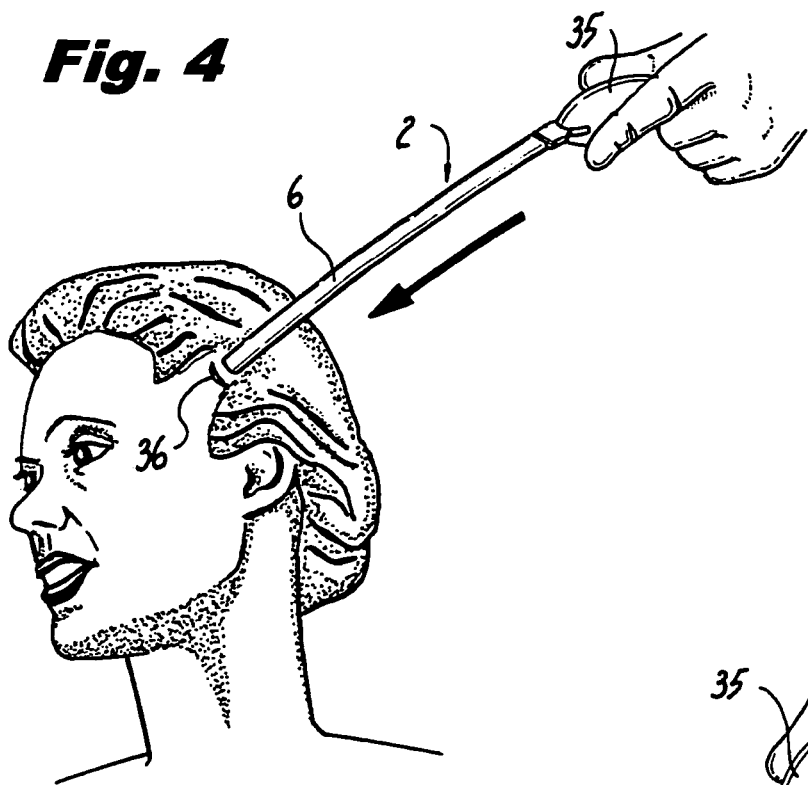
FIG. 4 is a pictorial illustration of the self-anchoring tissue lifting device formed in accordance with the present invention oriented to treat a midface abnormality.

The self-anchoring tissue lifting device 2 of the present invention is illustrated by FIGS. 1-3 and 8 of the drawings. It will be seen from the drawings that a self-anchoring tissue lifting device 2 constructed in accordance with the present invention includes an implant 4 and a removable foil cover 6 disposed on the implant 4.

Initially referring to FIGS. 1-3 of the drawings, it will be seen that a self-anchoring tissue lifting device 2 used for facial reconstructive surgeries or for the treatment of facial abnormalities and deformities basically includes an implant 4 and a removable foil cover 6 disposed on the implant 4. The implant 4 preferably includes an elongated, relatively thin, generally planar, mesh main body or strip 8 having a distal end 10 and a proximal end 11 situated longitudinally opposite the distal end 10. The mesh strip 8 also includes opposite top and bottom surfaces 12, 14, and opposite lateral edges 16, each of the top and bottom surfaces 12, 14 and lateral edges 16 being situated along the longitudinal length of the mesh main body or strip 8 between the distal end 10 and the proximal end 11 thereof.

As will be described in greater detail, the mesh material used in the mesh strip 8 is preferably a tissue ingrowth promoting mesh, such as that commonly referred to by the trademark ULTRAPRO® manufactured by Ethicon GmbH, Norderstedt or even more preferably, a reinforced version of the ULTRAPRO® mesh material. This material is a reinforced mesh made from Prolene® threads (polypropylene monofilament) and MONOCRYL® threads (polyglecaprone monofilament) in a ratio of about 40/60 weight/weight. The reinforced mesh preferably has a ratio of bioabsorbable to non-bioabsorbable components which is about 60/40 percent. This ratio is preferred, as it meets the requirements for initial tactile feedback of the mesh for correct placement by the surgeon, and the necessary softness after tissue ingrowth. The reinforced-mesh-structure described above is further preferred for use as the mesh-strip 8, as its pore sizes enable the ingrowth of tissue into the mesh without creating a scar or scar plates, and furthermore, the tissue in between the mesh pores will not becomes strangulated if the implant 4 is pulled due to movement of the patient's tissue to which the implant adheres. The preferred structure of the reinforced mesh material is disclosed in German Patent Publication No. DE 10 2005 012 555 B4, and European Patent Publication No. EP 1 700 579 A1, the disclosures of which are incorporated herein by reference.

The distal end 10 of the mesh main body 8 includes a tissue fixation tip 18 mounted thereon. The tissue fixation tip 18 may be in the form of a fleece material 20, such as that commonly referred to by the trademark ETHISORB® manufactured by Ethicon GmbH, Norderstedt. The tissue fixation tip 18 can easily become attached to the tissue of a patient upon its contact therewith.

FIG. 3 illustrates in greater detail the structure of the distal end 10 of the implant portion 4 of the self-anchoring tissue lifting device 2 of the present invention. It will be seen from FIG. 3 that a sandwich or laminate 22 is formed at the distal end 10 of the implant 4, which includes a layer of ETHISORB® material 20, having a ratio of about 7:1 of VICRYL® polyglactin synthetic absorbable threads (preferably, polyglaction 910, 28 den) to PDS® (polydioxonane threads, 30 den) material, thermally bonded to one or both of the top and bottom sides 12, 14 of the mesh strip 8 using a thin layer of PDS® (polydioxonane) film 24 having a thickness on the order of about 25 μm. Thus, the separate layers at the distal end 10 of the implant 4 of the laminate 22 which is formed would preferably be the following: ETHISORB® (7:1) fleece 20; a PDS® film layer 24 having a thickness on the order of about 25 μm; the ULTRAPRO®-reinforced mesh strip 8, having a ratio of MONOCRYL® threads to Prolene® threads on the order of about 60:40 percent; another layer of PDS® film 24 having a thickness on the order of about 25 μm; and finally, another layer of ETHISORB® (7:1) fleece 20. During the manufacturing process, the PDS® films 24 melt completely and will bond the ETHISORB® fleece material 20 on both sides of the mesh strip 8 together through the pores of the mesh. The preferred temperature for forming the laminate 22 is about 105° Celsius applied at a duration of about 2 min (by a pair of heated plates (not shown) spaced apart from one another by about 1.2 millimeters.

Figure 8:
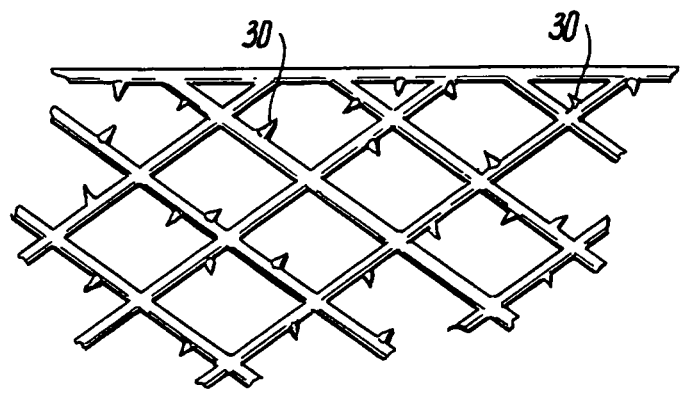
FIG. 8 is an enlarged side view of a portion of the self-anchoring tissue lifting device formed in accordance with the present invention.
Figure 9:
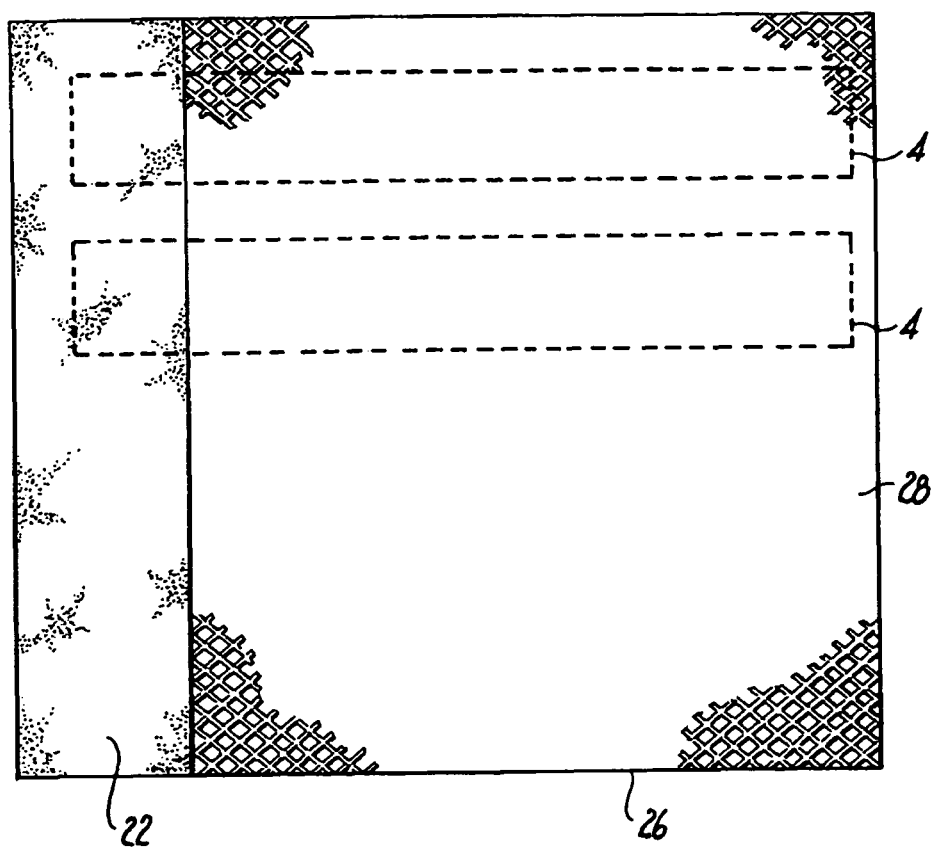
FIG. 9 is a top view of a sheet of material from which the self-anchoring tissue lifting device formed in accordance with the present invention is formed in accordance with a manufacturing process of the present invention.

The results of this process is shown in FIG. 9 of the drawings, where the sandwiched or laminated area 22 is situated on one side of the mesh material sheet 26, with the mesh material 28 situated adjacent the sandwiched area 22. The sandwiched mesh sheet 26 is then cut into individual implants 4 using a mechanical cutting device, or more preferably, a laser cutting unit. By cutting the mesh implants 4 using a laser, the fiber or thread ends of the mesh are melted together as a consequence of the process. This is advantageous, as it provides the mesh implant 4 with a superior stiffness and improves the anchoring of the mesh into the tissue by creating small tissue engaging "prickles" 30 along the lateral edges 16 of the mesh strip 8 which are formed by the cut transverse threads of the mesh material, as illustrated by FIG. 8 of the drawings.

The proximal end 11 of the mesh strip 8 of the implant 4 preferably has no tissue fixation tip 18 (i.e., the ETHISORB® fleece material 20) situated thereat like that at the distal end 10, other than the mesh material itself and the "prickles" 30 formed on the lateral edges 16 of the mesh strip 8. It may seem counterintuitive that a mesh implant with only one fixation end (i.e., the distal end 10 of the implant 4) can completely fix a relatively long mesh strip in a desired position; however, because of the tissue engaging prickles. 30 situated along the longitudinal length of the implant 4, in combination with the ETHISORB® fixation material. 20 situated at the distal end 10 of the implant 4, reliable initial fixation and continuous adjustment of the human facial tissue along the complete length of the implant 4 is made possible with the structure of the tissue lifting device 2 of the present invention described above.

The preferred width of the mesh implant 4, measured across the mesh strip 8, is preferably about 10 millimeters to about 11 millimeters, while the length of the implant 4, from the distal end 10 to the proximal end 11, is preferably about 190 millimeters to about 200 millimeters. The tissue fixation tip 18, situated at the distal end 10 of the mesh strip 8, has a preferred length of about 15 millimeters. With this preferred structure, the implant 4 is able to resist pulling forces along the longitudinal axis thereof and keep its original shape even under tension. A narrowing of conventional mesh implants, i.e., a decrease in the width of the mesh, under mechanical strain could lead to the implant slipping relative to the tissue, thus impairing the effect of the procedure. This "narrowing" of conventional mesh implants, which is also commonly known as mesh "roll in" and "string formation", is detrimental to the intended use of the implant. With the present invention, dimensioned as described above, no roll in or taper of the mesh implant 4 under tension occurs. While the fleece fixation material 20 at the distal end 10 of the implant 4 keeps the implant end in place, the implant 4 can be adjusted with respect to the tissue under tension. The tissue engaging prickles 30 along the lateral edges 16 of the mesh strip 8 will hold the tissue along the length of the implant 4 under tension in the adjusted position, and the new distribution of the tissue along the length of the implant, i.e., the "lifting effect", which is only achieved when the tissue is under tension, can be sustained permanently by preventing the implant 4 from narrowing due to the structure of the mesh material and the dimensions of the implant described above.

The ULTRAPRO® reinforced mesh material is preferred for use as the mesh strip 8 of the implant 4, as the mesh pore size will not essentially be changed under tension. This is important, because if the pores are too small (that is, less than about 1 millimeter), this may lead to a "bridging" of connective tissue across the pores, possibly resulting in high contractile forces. These contractile forces will endanger the aesthetic outcome of the procedure and may even require ex-plantation (i.e., the removal of the implant).

The ULTRAPRO® reinforced mesh material is also preferably used for the mesh strip 8 of the implant 4, as the entire mesh strip, not only the anchoring distal end 10 of the implant, is initially relatively stiff and resistant to pull forces. This also enables the surgeon to recognize the position of the mesh implant 4 by tactile feedback during its passage below or through the subcutaneous tissue, which is not visible to the surgeon. Also, after tissue ingrowth, the mesh implant 4 is very soft and cannot be felt or seen through the skin, which is very important in facelift procedures. Due to the structure of the mesh implant 4 as described above, the implant can comply to facial movement without resulting in a foreign body sensation to the patient.

The proximal end 11 of the mesh implant 4 may be cut without fraying, due to the mesh structure of the material used for the mesh strip 8. Furthermore, if desired, the proximal end 11 may include a tissue fixation tip 18 situated thereat, like the ETHISORB® fleece material 20 situated at the distal end 10 of the mesh strip 8. Alternatively, the proximal end 11 of the mesh strip 8 may be fixated to the tissue by using clips or sutures.

As can be further seen from FIGS. 1 and 2 of the drawings, the distal end 10 of the mesh strip 8 and the fixation tip laminate 22 may be formed with barbs 32 extending outwardly from the opposite lateral edges 1 fixation tip 6 of the implant 4 (or mesh strip 8). The barbs 32 further help in anchoring the implant to the patient's facial tissue. Also, as can be seen from FIGS. 1 and 2, the distal end 10 of the implant 4 may include a central opening or slot 34 formed through the thickness of the laminate 22 (i.e., the mesh strip 8 and the tissue anchoring fleece material 20 situated on the top and bottom surfaces 12, 14 of the mesh strip 8 at the distal end 10 thereof). The slot 34 is provided to receive a member of an applicator tool 35, on which the tissue lifting device 2 of the present invention may be removably mounted during the initial device deployment and positioning phases of the surgical procedure.

A preferred method of manufacturing the implant 4 of the tissue lifting device 2 of the present invention will now be described. A section of the preferred ULTRAPRO® reinforced mesh material is scoured and annealed by spreading it on a rack under a static tension at an annealing temperature of about 128° Celsius, plus or minus about 40 Celsius, for an annealing duration of about 6 hours plus or minus about 15 minutes.

In accordance with the sandwiching process, the ETHISORB® fleece anchoring material 20, which is preferably composed of VICRYL® sutures or threads and PDS® in a preferred ratio of about 7:1, is thermally bonded to the top and bottom sides 12, 14 of the mesh strip 8 with a thin layer of PDS® film 24 on each side of the mesh strip 8, as described previously. The sandwiching temperature is preferably about 105° Celsius, the duration of the sandwiching process is about 2 min, and the distance between the heated plates used in the sandwiching process is about 1.2 millimeters, as described previously.

The removable foil cover 6 wraps about the implant 4, at least along a portion of the longitudinal length of the mesh strip 8 thereof, to prevent the adhesion of the implant 4 to the patient's body tissue during the initial phases of the deployment and proper positioning of the implant.

The preferred methods of surgically treating a patient's midface, jowl and cervical areas using the self-anchoring tissue lifting device of the present invention are illustrated in FIGS. 4-7 of the drawings, and will now be described in detail.

Figure 5:
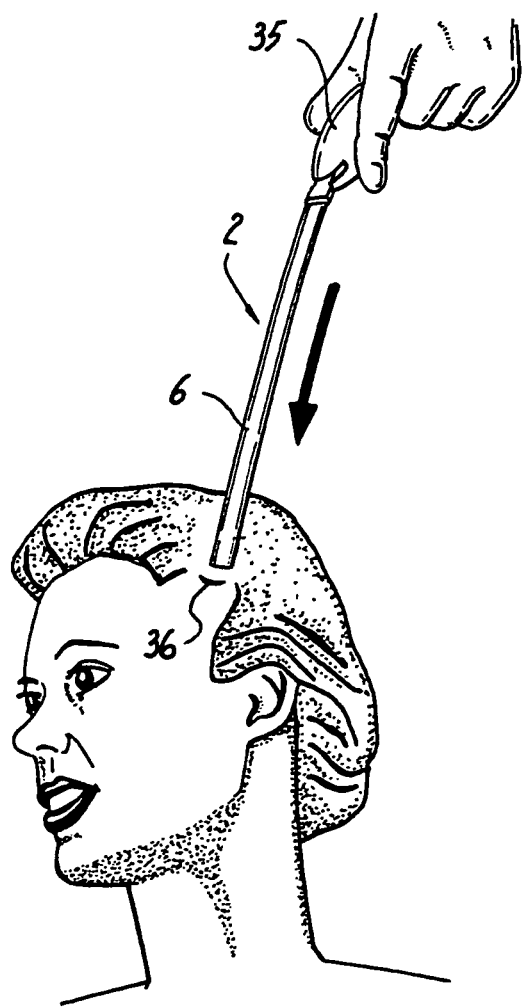
FIG. 5 is a pictorial illustration of the self-anchoring tissue lifting device formed in accordance with the present invention oriented to treat a jowl abnormality.

For treating the midface and jowl, a stab incision 36 is made within the hairline of the temple region, and the device 2 is applied from the temporal area to the peak of the ipsilateral cheek to capture the malar fat pad in treating a midface abnormality, as shown in FIG. 4 of the drawings, or the ptotic tissue causing the jowl, as shown in FIG. 5.

For treating a neck tissue abnormality, the device 2 is applied to a stab incision 36 through or below the subcutaneous tissue plane from behind the patient's ear to the ipsilateral submental area, as illustrated by FIGS. 6A-6C of the drawings. The distal end 10 of the mesh implant 4, at which end the ETHISORB® fleece anchor material 20 is situated, is then located in the submental area, i.e., the mouth floor close to the chin, while the proximal end 11, still covered with the foil cover 6, comes to a position at the patient's mastoid, as shown in FIGS. 6F and 7.

Figure 7:
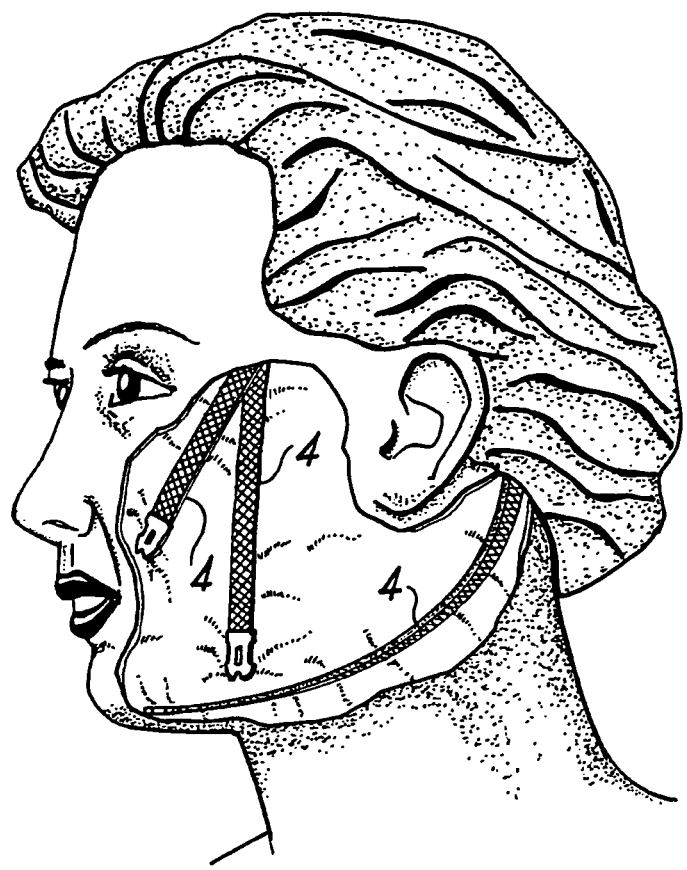
FIG. 7 is a semi-transparent illustration showing the positions the self-anchoring tissue lifting device formed in accordance with the present invention may occupy in treating various facial abnormalities.

With respect to the cervical application of the tissue lifting device 2 of the present invention, when the distal end 10 of the mesh implant 4 is released from the applicator tool 35, as illustrated by FIG. 6D, and brought under slight tension by some backtracking of the skin, as illustrated by FIG. 6E, the tissue fixation tip 18 at the distal end 10 of the mesh strip 8 of the implant 4 will interlock with the septae (vertical fascias) of the subcutaneous tissue layer, as can be seen from FIG. 7 of the drawings.

After the applicator tool 35 has been removed, the foil cover 6, which preferably covers most of the mesh strip 8 except the tissue anchoring distal end 10 thereof which is now laying submentally, at the naso-labial fold or at the jowl, is gradually pulled away from the implant 4 and out from within or beneath the subcutaneous tissue layer, as shown by FIGS. 6E and 7 of the drawings, while the ptotic soft tissue is shifted according to a vector that points toward a backward and upward direction relative to the patient's face. With the simultaneous tissue shift during the removal of the foil cover 6 and freeing of the mesh implant 4 therefrom, the proximal end 11 of the mesh implant is shifted from its initial position to a more upward facial position and, when uncovered by the foil cover 6, interlocks with the patient's tissue thereat. Thus, the tissue is captured at or close to its original position, as illustrated by FIGS. 6F and 7.

When the foil cover 6 covering the exposed mesh strip 8 of the implant 4 is removed, the lateral edges 16 of the mesh strip 8 and texture of the top and bottom surfaces 12, 14 of the mesh strip engage the surrounding subcutaneous tissue at the cut mesh thread ends which define the tissue engaging prickles 30, which act as barbs that interlock with the tissue itself, creating sufficient resistance between the implant 4 and the patient's tissue. The gross texture of the mesh strip top and bottom surfaces 12, 14 supports this effect and provides additional friction to the implant. Optionally, the proximal end 11 of the implant can be fixated to the patient's tissue using sutures or staples.

The self-anchoring tissue lifting device 2 and method of using the device for facial cosmetic reconstructive surgery avoid the inherent disadvantages of known facial cosmetic reconstructive surgery methods and devices. The implant 4 is applied with a minimally invasive procedure and avoids the creation of a scar plate. The structure of the implant 4 allows it to be adjusted along its length for proper positioning. Furthermore, the implant 4 is not visible nor tactilely noticeable after tissue ingrowth has occurred. The method of facial reconstructive surgery using the self-anchoring tissue lifting device 2 of the present invention is simplified and less time consuming than conventional procedures.

Although illustrative embodiments of the present invention have been described herein with reference to the accompanying drawing, it is to be understood that the invention is not limited to those precise embodiments, and that various other changes and modifications may be effected therein by one skilled in the art without departing from the scope or spirit of the invention.

What is claimed is:

1. A method of facial reconstructive surgery using a self-anchoring tissue lifting device, which comprises an elongated mesh strip having a distal end and a proximal end situated longitudinally opposite the distal end, opposite top and bottom surfaces and opposite lateral edges, the top and bottom surfaces and the lateral edges being situated along a longitudinal length of the mesh strip between the distal end and the proximal end thereof, the device further having a tissue fixation portion situated at the distal end of the mesh strip, and a tissue engaging structure situated on the opposite lateral edges of the mesh strip, the tissue engaging structure including prickles that extend along the full longitudinal length of the mesh strip for holding the full longitudinal length of the mesh strip under tension, and a cover wrapped about the mesh strip at least along a portion of the longitudinal length thereof and being removable therefrom, the method comprising the steps of: cutting a sheet of mesh material to form said elongated mesh strip, and wherein the cutting step creates the prickles along the lateral edges of said elongated mesh strip that are formed by cut threads of said mesh material;

forming a stab incision within the hairline of a temple region of a patient;

inserting, by use of an applicator tool, the self-anchoring tissue lifting device through the stab incision;

navigating the device, by way of the applicator tool, at least one of through and below the subcutaneous tissue layer of the patient's face;

directing, with the applicator tool, the tissue fixation portion at the distal end of the mesh strip from the temporal area to the peak of the ipsilateral cheek of the patient's face to engage at least one of the malar fat pads to treat midface abnormalities and the ptotic tissue causing a jowl in the patient's face;

releasing the tissue fixation portion from the applicator instrument and removing the applicator instrument from the stab incision, wherein the tissue fixation portion, the mesh strip and the cover remain implanted in the subcutaneous tissue as the applicator instrument is removed from the stab incision; and after removing the applicator instrument, removing the cover of the self-anchoring tissue lifting device from the stab incision and away from the mesh strip to expose the mesh strip to the subcutaneous tissue surrounding the mesh strip, wherein the tissue fixation portion and the mesh strip remain implanted in the subcutaneous tissue as the cover is removed from the stab incision.

2. A method of facial reconstructive surgery as defined by claim 1, wherein said cover is a foil cover.

3. A method of facial reconstructive surgery using a self-anchoring tissue lifting device including an elongated mesh strip having a distal end and a proximal end situated longitudinally opposite the distal end, opposite top and bottom surfaces and opposite lateral edges, the top and bottom surfaces and the lateral edges being situated along a longitudinal length of the mesh strip between the distal end and the proximal end thereof, the device further having a tissue fixation portion situated at the distal end thereof, and a tissue engaging structure situated on the opposite lateral edges of the mesh strip, the tissue engaging structure including prickles that extend along the full longitudinal length of the mesh strip for holding the full longitudinal length of the mesh strip under tension, and a cover being wrapped about the mesh strip at least along a portion of the longitudinal length thereof and being removable therefrom, wherein the tissue fixation portion situated at the distal end of the mesh strip includes a tissue engaging fleece material mounted to at least one of the top and bottom surfaces of the mesh strip, the device being removably mounted on an applicator tool, the method comprising the steps of: cutting a sheet of mesh material to form said elongated mesh strip, and wherein the cutting step creates the prickles along the lateral edges of said elongated mesh strip that are formed by cut threads of said mesh material;

forming a stab incision through the subcutaneous tissue plane from behind an ear of a patient;

inserting the self-anchoring tissue lifting device through the stab incision using the applicator tool;

navigating the self-anchoring tissue lifting device, by way of the applicator tool, at least one of through and below the subcutaneous tissue layer of the patient's face;

directing, with the applicator tool, the tissue fixation portion at the distal end of the mesh strip from the stab incision behind the patient's ear through the ipsilateral submental area whereby the tissue fixation portion situated at the distal end of the mesh strip is located in the submental area of the patient's face and so that the proximal end of the mesh strip and the cover wrapped about the mesh strip are situated at a position at the mastoid of the patient's face;

releasing the tissue lifting device from the applicator tool and removing the applicator tool from the patient's face, wherein the tissue fixation portion, the elongated mesh strip and the cover remain implanted in the subcutaneous tissue layer as the applicator instrument is removed from the stab incision;

tensioning the distal end of the mesh strip so that the tissue fixation portion situated thereat will lockingly engage the septae of the subcutaneous tissue layer; and after removing the applicator tool, removing the cover wrapped about the mesh strip to pull the cover out of the stab incision, expose the mesh strip to the patient's tissue and to allow the mesh strip to interlock therewith.

4. A method of facial reconstructive surgery as defined by claim 3, which further comprises the step of:

shifting the ptotic soft tissue of the patient in a backward and upward direction relative to the patient's face simultaneously with the step of removing the cover.

5. A method of facial reconstructive surgery as defined by claim 3, wherein the step of tensioning the distal end of the mesh strip includes the step of tensioning the distal end of the mesh strip by pulling the patient's skin backward.

6. A method of facial reconstructive surgery as defined by claim 3, which further comprises the step of:

after removing the cover, shifting the proximal end of the mesh strip from an initial position to a more upward position relative to the patient's face and allowing the mesh strip to engage and interlock with the tissue of the patient at the more upward position.

7. A method of facial reconstructive surgery as defined by claim 6, which further comprises the step of:

fixating the proximal end of the mesh strip to the patient's tissue at the more upward position relative to the patient's face by using at least one of a suture and a staple.

8. A method of facial reconstructive surgery as defined by claim 3, wherein said cover is a foil cover.

9. A method of facial reconstructive surgery comprising:

providing a self-anchoring tissue lifting device including an elongated mesh strip having a proximal end, a distal end, and a tissue fixation tip secured to the distal end of said elongated mesh strip wherein the step of providing a self-anchoring tissue lifting device comprises cutting a sheet of mesh material to form said elongated mesh strip, and wherein the cutting step creates tissue engaging prickles along lateral edges of said elongated mesh strip that are formed by cut threads of said mesh material;

providing an applicator instrument that selectively secures and releases said tissue fixation tip;

providing a cover wrapped about the proximal end of said elongated mesh strip, wherein said tissue fixation tip is exposed outside said cover;

forming an incision in a patient;

securing said tissue fixation tip with said applicator instrument;

using said applicator instrument to pass said tissue fixation tip through the incision and implanting said tissue fixation tip, said elongated mesh strip and said cover in subcutaneous tissue;

releasing said tissue fixation tip from said applicator instrument and removing said applicator instrument from the incision, wherein said tissue fixation tip, said elongated mesh strip and said cover remain implanted in the subcutaneous tissue as said applicator instrument is removed from the incision;

pulling said cover out of the incision and away from said elongated mesh strip to expose the proximal end of said elongated mesh strip to the subcutaneous tissue surrounding said elongated mesh strip, wherein said tissue fixation tip and said elongated mesh strip remain implanted in the subcutaneous tissue as said cover is removed from the incision.

10. The method as claimed in claim 9, wherein the incision is formed in the patient's face, and wherein the implanting step comprises using said applicator instrument for directing said tissue fixation tip from a temporal area to a peak of an ipsilateral cheek of the patient's face to engage at least one malar fat pad.

11. The method as claimed in claim 10, further comprising shifting ptotic soft tissue in a backward and upward direction relative to the patient's face when pulling said cover out of the incision.

12. The method as claimed in claim 9, wherein said cover comprises a foil cover.

13. The method as claimed in claim 9, wherein the incision is formed in the patient's face, and wherein the step of passing said tip through the incision comprises directing said tissue fixation tip through the incision so that said tissue fixation tip is located in a submental area of the patient's face and the proximal end of said elongated surgical mesh is located at the mastoid of the patient's face.

14. The method as claimed in claim 9, wherein said elongated mesh strip has a length of about 190-200 mm and a width of about 10-11 mm.

15. The method as claimed in claim 9, wherein said tissue fixation tip comprises fleece and has a length of about 15 mm.

16. The method as claimed in claim 9, wherein said tissue fixation tip has a central opening adapted to receive a member of said applicator instrument for securing said applicator instrument to said tissue fixation tip when passing said tip through the incision.

* * * * *